(12) United States Patent
Miner

(10) Patent No.: US 8,216,186 B2
(45) Date of Patent: Jul. 10, 2012

(54) CATHETER DEVICE WITH HOODING FEATURE

(75) Inventor: Tom M. Miner, Alpine, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 12/721,266

(22) Filed: Mar. 10, 2010

(65) Prior Publication Data

US 2011/0224617 A1 Sep. 15, 2011

(51) Int. Cl.
*A61M 5/178* (2006.01)
(52) U.S. Cl. .............................. 604/164.08; 604/164.07
(58) Field of Classification Search ............... 604/93.01, 604/164.01, 164.06–164.08, 263, 158, 164.12, 604/170.01–170.03
See application file for complete search history.

(56) References Cited

U.S. PATENT DOCUMENTS

| | | | |
|---|---|---|---|
| 4,231,367 A | 11/1980 | Rash | |
| 4,966,586 A | 10/1990 | Vaillancourt | |
| 5,092,842 A | 3/1992 | Bechtold et al. | |
| 5,156,792 A | 10/1992 | Holdaway et al. | |
| 5,201,712 A | 4/1993 | Bryant | |
| 5,330,432 A * | 7/1994 | Yoon | 604/164.12 |
| 5,447,501 A | 9/1995 | Karlsson et al. | |
| 5,665,072 A * | 9/1997 | Yoon | 604/164.12 |
| 5,827,221 A * | 10/1998 | Phelps | 604/506 |
| 5,865,806 A * | 2/1999 | Howell | 604/164.12 |
| 6,287,278 B1 | 9/2001 | Woehr et al. | |
| 6,461,362 B1 | 10/2002 | Halseth et al. | |
| 6,527,747 B2 | 3/2003 | Adams et al. | |
| 6,814,725 B2 | 11/2004 | Gutierrez | |
| 7,192,433 B2 | 3/2007 | Osypka et al. | |
| 7,264,613 B2 | 9/2007 | Woehr et al. | |
| 7,691,093 B2 | 4/2010 | Brimhall | |
| 7,736,340 B2 | 6/2010 | Harding et al. | |
| 7,744,567 B2 | 6/2010 | Glowacki et al. | |
| 2003/0199827 A1 | 10/2003 | Thorne | |
| 2004/0243061 A1 | 12/2004 | McGurk | |
| 2005/0004524 A1 * | 1/2005 | Newby et al. | 604/164.08 |
| 2005/0080378 A1 | 4/2005 | Cindrich et al. | |
| 2005/0090801 A1 * | 4/2005 | Racz et al. | 604/500 |
| 2005/0131350 A1 * | 6/2005 | Shaw et al. | 604/168.01 |
| 2006/0041231 A1 * | 2/2006 | Pressly et al. | 604/164.08 |
| 2006/0161108 A1 * | 7/2006 | Mogensen et al. | 604/164.01 |
| 2007/0078437 A1 | 4/2007 | Borden et al. | |
| 2008/0306452 A1 * | 12/2008 | Crawford | 604/263 |
| 2010/0204652 A1 * | 8/2010 | Morrissey et al. | 604/164.08 |
| 2011/0112511 A1 * | 5/2011 | Singer | 604/512 |

* cited by examiner

*Primary Examiner* — Victoria P Campbell
(74) *Attorney, Agent, or Firm* — Mony R. Ghose; Kirton & McConkie

(57) ABSTRACT

An intravenous catheter device having features to aid a user in hooding the beveled portion of an introducer needle during the catheterization process. An intravenous catheter device is modified to include a biasing arm capable of advancing a portion of the catheter device to cause a beveled portion of an introducer needle to be hooded within an interior lumen of the catheter tube. The dimensions of the biasing arm and various other interacting surfaces of the catheter device are configured to achieve effective hooding of the needle tip while avoiding overhooding or underhooding inaccuracies.

12 Claims, 10 Drawing Sheets

CATHETER DEVICE WITH HOODING FEATURE

BACKGROUND OF THE INVENTION

The present application relates generally to an intravenous catheter device having features to aid a user in hooding the beveled portion of an introducer needle during the catheterization process.

Various types of medical devices employ a needle for piercing the skin of a patient for diagnostic or therapeutic purposes. One such device is an over-the-needle intravenous catheter device. This device is commonly used as a means for inserting a flexible or semi-flexible catheter into a patient's blood vessel. Since the flexible or semi-flexible catheter is incapable of piercing the patient's skin, an introducer needle is inserted through the lumen of the catheter such that a beveled or working portion of the needle is exposed beyond the tip of the catheter. The patient's vasculature is accessed as the beveled portion of the needle is inserted through the patient's skin and into the targeted vein. The catheter and needle are then advanced into the vein until the desired position of the catheter is achieved. Once the catheter is properly positioned, the introducer needle is removed from the catheter and disposed.

In some instances, the diameter of the targeted vein is relatively small as compared to the gauge of the introducer needle. Thus, it is not uncommon for the beveled portion of the needle to breach or otherwise damage the targeted vein while advancing the catheter and needle into the vein. Accordingly, it is a common practice to "hood" the needle once the targeted vein has been accessed via the introducer needle and tip of the catheter. The process of hooding the needle involves maintaining a stationary position of the partially inserted catheter while simultaneously withdrawing the beveled portion of the needle into the inner lumen of the catheter. Once the needle tip has been hooded, the catheter is then advanced into the vein to a desired position. With the needle tip hooded, there is no danger of damaging the patient's vein while advancing the catheter.

Current methods for hooding the needle tip generally rely on a user's experience and/or estimation regarding the position of the needle tip relative to the tip of the catheter. Since the needle tip and catheter tip are both subcutaneously located, it is impossible for the user to see the position of the needle tip. Accordingly, users will typically withdrawal the needle from the catheter until the user believes that the needle tip is hooded. A result of this is that the needle tip is either underhooded or overhooded.

Where the needle tip is underhooded, the needle tip is not completely withdrawn into the lumen of the catheter. As such, a portion of the needle's bevel remains exposed thereby maintaining a risk of damage to the patient's vein. Where the needle tip is overhooded, the needle tip is overdrawn into the lumen of the catheter thereby leaving an extended portion of the catheter tip unsupported by the needle. Overhooding the needle tip is undesirable due the possibility of kinking, bending or otherwise obstructing the flow of the catheter while advancing the catheter into the patient's vein.

Thus, while techniques currently exist that are used to hood the beveled portion of a catheter during catheterization procedures, challenges still exist. Accordingly, it would be an improvement in the art to augment or even replace current techniques with other techniques.

BRIEF SUMMARY OF THE INVENTION

The present application relates generally to an intravenous catheter device having features to aid a user in hooding the beveled portion of an introducer needle during the catheterization process. In some embodiments, the catheter device includes a catheter adapter configured to support an intravenous catheter tube. The catheter device further includes a needle hub for supporting an introducer needle, a portion of the introducer needle extending through an inner lumen of the catheter adapter and the catheter tube, such that the beveled portion of the needle extends beyond a tip portion of the catheter tube. A portion of the needle hub is further configured to partially insert within the inner lumen of the catheter adapter, whereby the needle hub and the catheter adapter form an integral device.

The needle hub further includes a biasing arm. The biasing arm is provided as a means of advancing the catheter adapter in a distal direction relative to the needle hub. The biasing arm is generally an extended or elongated portion of the needle hub having a first end attached to the needle hub, and a second end positioned adjacent to an opposing surface of the catheter adapter. In some embodiments, the biasing arm includes an arched or non-linear profile such that the length of the biasing arm is greater than the linear distance between the first end of the biasing arm and the opposing surface of the catheter adapter. Some embodiments of the present invention include a single biasing arm. Other embodiments of the present invention include multiple biasing arms.

The biasing arm in accordance with the present invention includes an unactuated position and an actuated position. The unactuated position is generally characterized by the beveled portion of the introducer needle being exposed beyond the tip of the catheter tube. Conversely, the actuated position of the biasing arm is characterized by the beveled portion of the introducer needle being hooded or withdrawn into the inner lumen of the catheter tube. Prior to catheterization, the biasing arm is provided in an unactuated position such that the beveled portion of the needle is available to gain access to the vasculature of a patient. Once the patient's vasculature is accessed, the biasing arm is then actuated by pinching or compressing the biasing arm to temporarily remove the arched or non-linear profile of the arm. This causes the second end of the biasing arm to contact the opposing surface of the catheter adapter thereby advancing the catheter adapter in a distal direction, relative to the position of the needle hub. As the catheter tube is advanced in a distal direction, the beveled portion of the introducer needle is hooded within the catheter tube. As such, the possibility of damaging the patient's vein with the beveled portion of the needle is eliminated during further insertion of the catheter tube.

In some embodiments, the biasing arm includes a paddle grip having a channel or groove for seating a y-port of the catheter adapter. The groove is configured so as to permit the y-port to slidably shift within the groove between unactuated and actuated positions. In some embodiments an exposed surface of the y-port includes a texture to aid in gripping the y-port with a portion of the user's thumb. In other embodiments, an exposed surface of the paddle grip includes a texture to aid in gripping the biasing arm with a portion of the user's thumb. Prior to catheterization, the y-port is located within the groove such that the beveled portion of the needle is exposed beyond the tip of the catheter tube. Once the vasculature of the patient is accessed by the needle, the y-port is slid or shifted within the groove of the paddle grip thereby causing the beveled portion of the needle to be withdrawn into the inner lumen of the catheter tube. Unactuated and actuated positions of the catheter device are maintained via the user's thumb simultaneously contacting and thereby bridging the paddle grip and y-port portions of the needle hub and catheter adapter. Following final placement of the catheter tube, the paddle grip portion of the biasing arm is axially rotated such that the y-port is disengaged from the groove. The needle hub, biasing arm and introducer needle are then removed from the catheter adapter and discarded.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

In order to provide a thorough understanding of the invention, the following description discusses specific details. The skilled artisan, however, would understand that the invention can be practiced without employing these specific details. Indeed, the invention can be modified in any suitable manner and can be used in conjunction with any suitable chemical, apparatus, and technique conventionally used in the industry. Thus, the following more detailed description of the embodiments of the invention is not intended to be limiting in scope, but is merely representative of some presently preferred embodiments. Additionally, while the following discussion focuses on using the invention in health care settings, the antiseptic material may be used in any suitable setting.

Figure 1:
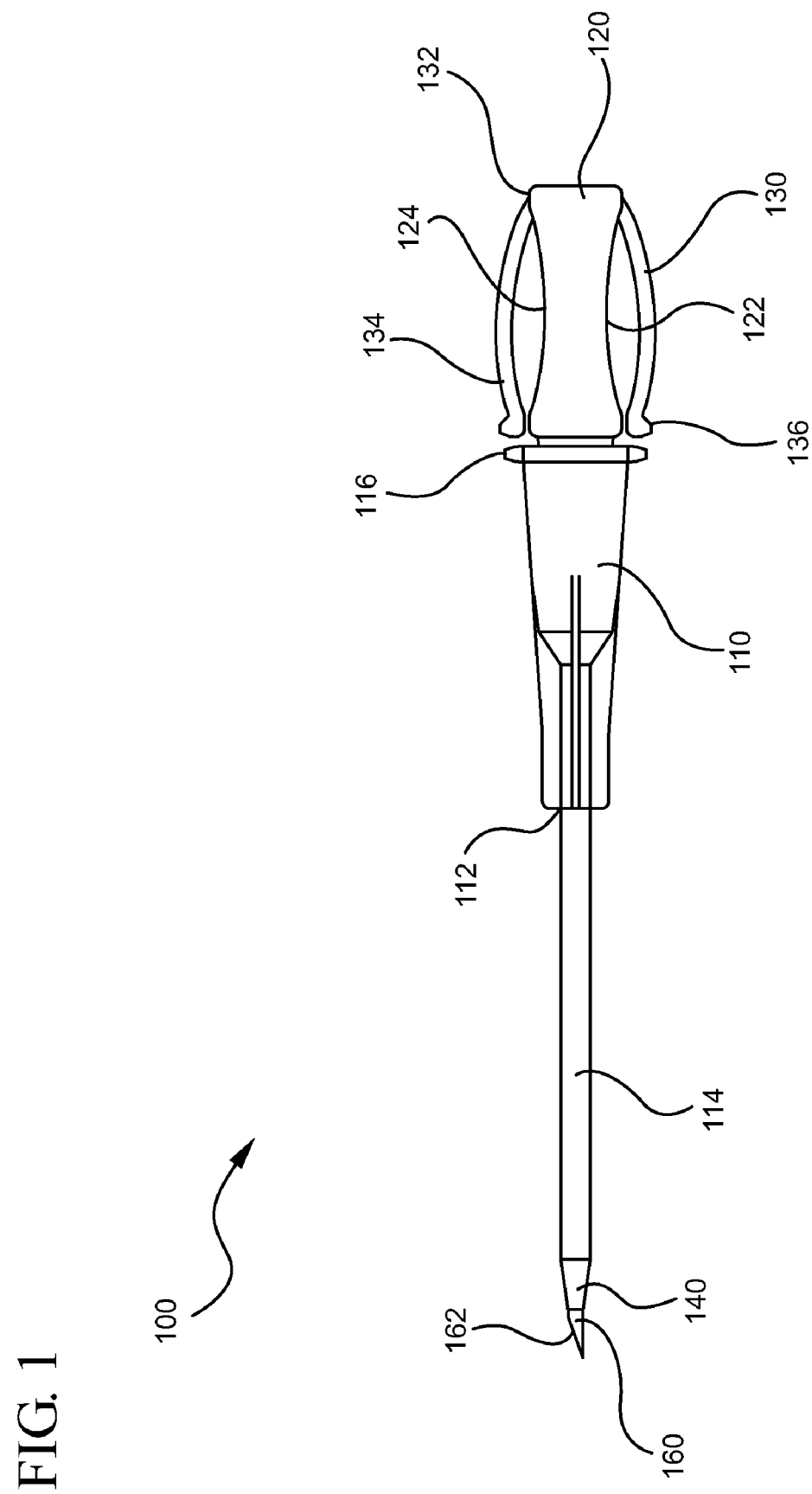
FIG. 1 is a side view of an intravenous catheter device in accordance with a representative embodiment of the present invention.

Referring now to FIG. 1, an intravenous catheter device 100 is shown. A catheter device 100 in accordance with the present invention generally comprises a catheter adapter 110 and a needle hub 120. The catheter adapter 110 generally includes a first end 112 configured to support a catheter tube 114. Catheter tube 114 is an over-the-needle catheter that is typically inserted into the vasculature of a patient. Alternately, in some embodiments catheter tube 114 is inserted into a body cavity, duct or vessel of a patient. Catheter tube 114 thereby allows for drainage, injection of fluids or access by surgical instruments into a desired portion of a patient. In some embodiments, catheter tube 114 is a thin, flexible tube that bends and conforms during the catheterization process. Catheter tube 114 may include a variety of polymer materials, including silicone rubber latex, Teflon®, polypropylene, and various thermoplastic elastomers.

Catheter adapter 110 generally comprises a rigid polymer material, such as polystyrene, polyvinyl acetate, polycarbonate and polymethyl methacrylate. Catheter adapter 110 generally includes an inner lumen whereby to receive or house a portion of needle hub 120. A first end 112 of the catheter adapter 110 is configured to compatibly receive catheter tube 114, whereby the catheter tube 114 and inner lumen of the catheter adapter 110 are in fluid communication. In some embodiments, catheter adapter 110 further includes an annular ridge 116 or flange forming a terminal end of the catheter adapter 110. Ridge 116 is generally provided as a structural feature to enable coupling of an extravascular components, such as a male luer, a syringe or a section of intravenous tubing. In some embodiments, ridge 116 comprises a set of threads to compatibly receive a complementary set of threads on an extravascular component or device.

The needle hub 120 is generally provided as a base means for securing a non-working end of an introducer needle 160. Needle hub 120 therefore may include any material, size, shape or configuration capable of forming a base for introducer needle 160. In some embodiments, a portion of needle hub 120 is housed within the inner lumen of catheter adapter 110, such that needle hub 120 and catheter adapter 110 form an integral device. An exposed portion of needle hub 120 is generally provided as a gripping surface whereby a user may grip the intravenous catheter device 100 and control the insertion thereof.

In some embodiments, needle hub 120 further includes a biasing arm 130. In some embodiments, needle hub 120 comprises a single biasing arm, as shown in FIGS. 3A through 6, below. In other embodiments, needle hub 120 comprises a plurality of biasing arms 130. Biasing arms 130 generally comprise a molded extension or feature of the needle hub 120 each having a first end 132 attached to the needle hub 120 and a second end 134 extending outwardly from the first end 132. In some embodiments, the second end 134 of each biasing arm 130 further includes a contact surface 136 configured and positioned in proximity to the annular ridge 116 of catheter adapter 110. Biasing arms 130 are generally arched or otherwise comprises a non-linear profile such that the length of each biasing arm 130 is greater than the distance between the first end 132 of each biasing arm 130 and the annular ridge 116 of the catheter adapter 110. In some embodiments a gripping surface 122 of the needle hub 120 is contoured or otherwise shaped to provide a gap 124 between each biasing arm 130 and the gripping surface 122.

Figure 2A:
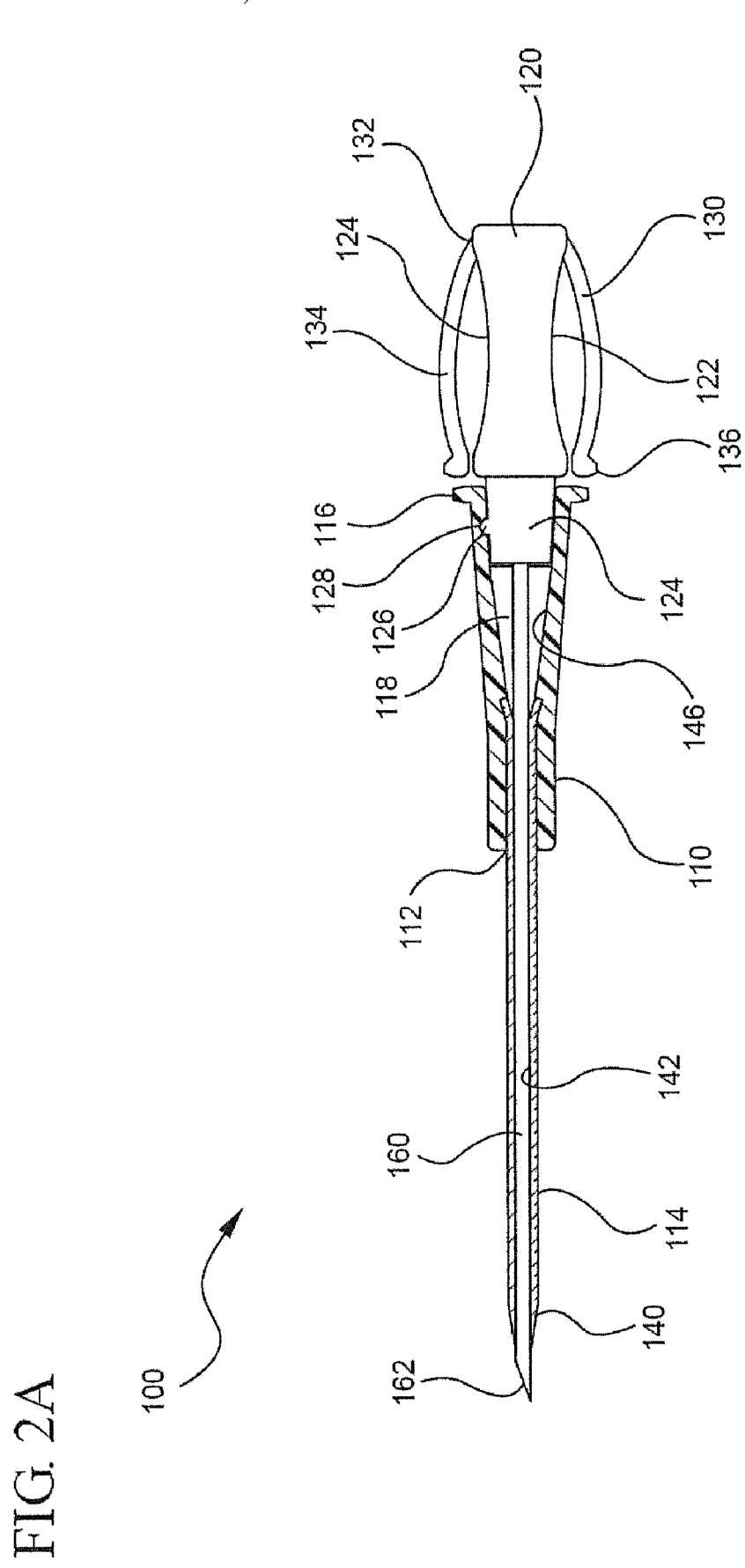
FIG. 2A is a partial cross-section side view of an intravenous catheter device in accordance with a representative embodiment of the present invention.

Referring now to FIG. 2A, a partially cross-sectioned side view of intravenous catheter device 100. Biasing arms 130 comprise both actuated and unactuated positions. The unactuated position is shown in FIG. 2A and is characterized by the unhooded position of the beveled portion 162 of the introducer needle 160. In some embodiments, the unhooded position of the introducer needle 160 is achieved when the inserted portion 124 of the needle hub 120 is fully housed within the inner lumen 118 of the catheter adapter 110. Thus, the unhooded position of the introducer needle 160 provides that the beveled or working portion 162 of the introducer needle 160 is exposed beyond the tip 140 of the catheter tube 114. As such, the bevel 160 of the needle 160 is unobstructed and therefore physically available to pierce the patient's skin to gain vascular access.

In some embodiments, the inserted portion 124 of the needle hub 120 further includes a feature 126 for engaging a detent 128 located on an inner surface 146 of the catheter adapter 110. The interaction between the feature 126 and the detent 128 prevents premature hooding of the needle 160 during catheterization. The interaction further prevents premature hooding of the needle 160 during assembly, packaging and shipment of the intravenous catheter device 100. In some embodiments, the inserted portion 124 of the needle hub 120 is modified to include a detent (not shown) configured to receive a feature (not shown) formed on the inner surface 146 of the catheter adapter 110. In other embodiments, feature 126 comprises an annular ridge and detent 128 comprises an annular groove or recess. One of skill in the art will appreciate that the interaction between a desired feature and a compatible detent will be sufficiently resilient to prevent premature hooding of the needle 160, yet be capable of defeat by user manipulation of biasing arms 130.

Figure 2B:
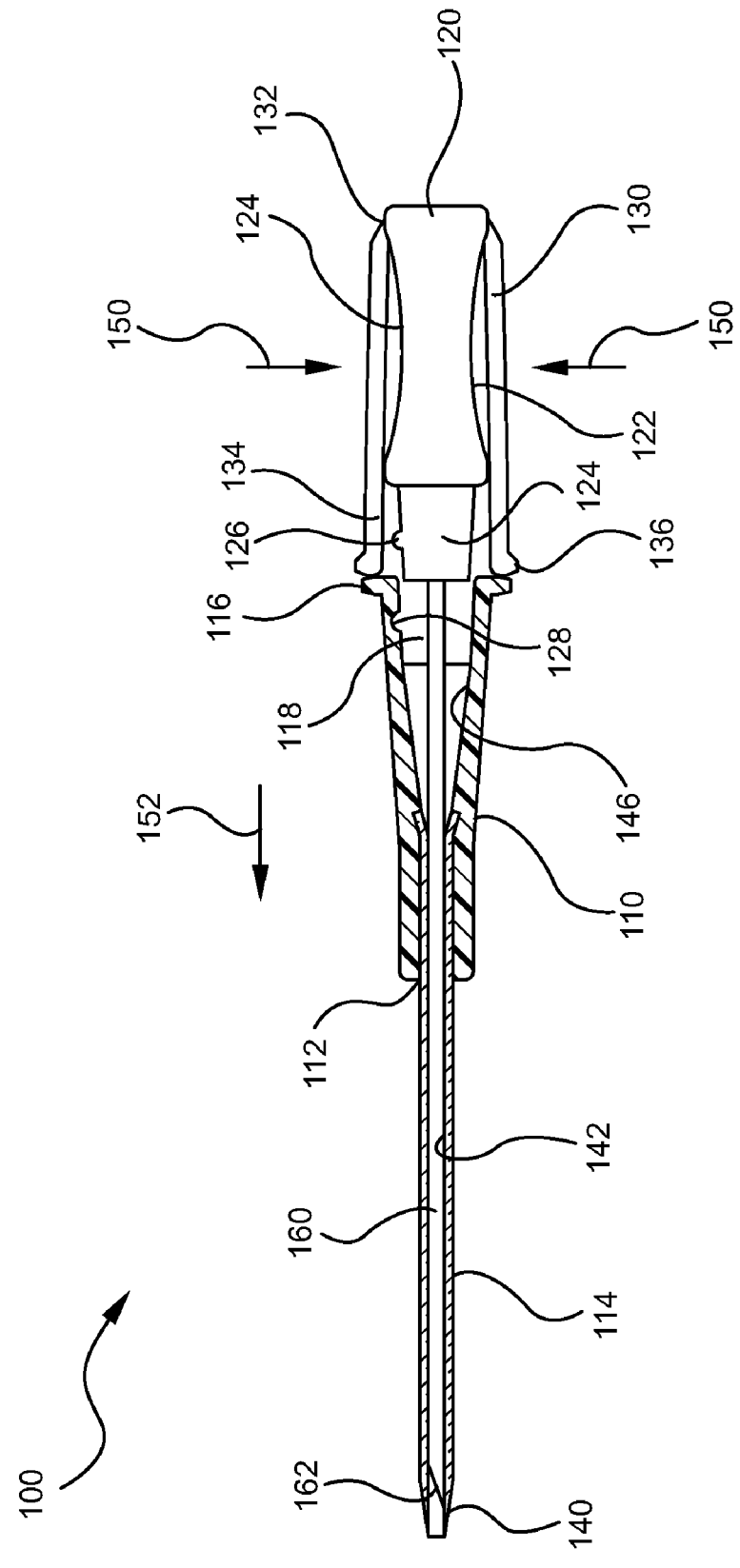
FIG. 2B is a partial cross-section side view of an intravenous catheter device following actuation of the biasing arms in accordance with a representative embodiment of the present invention.

Referring now to FIG. 2B, a partially cross-sectioned side view of the intravenous catheter device 100 is shown in an actuated position. An actuated position is characterized by the hooded position of the beveled portion 162 of the introducer needle 160. A hooded position is defined as a position of intravenous catheter device 100 wherein the beveled portion 162 of the introducer needle 160 is contained within lumen 142 of the catheter tube 114. In other words, the hooded position of the catheter device 100 is achieved when the beveled or working portion 162 of the introducer needle 160 is physically shielded within the catheter tube 114.

Prior to the catheterization of a patient, the biasing arms 130 of the intravenous catheter device 100 are provided in an unactuated position such that the beveled portion 162 of the introducer needle 160 is available to access the patient's vasculature. Once the beveled portion 162 of the introducer needle 160 accesses the patient's vasculature, biasing arms 130 are actuated by compressing or pinching 150 the arms 130 to temporarily remove the arch or non-linear profile of each arm 130. By temporarily removing the non-linear profile of each arm 130, the distance between the first end 132 and the second end 134 of each arm 130 is increased thereby repositioning the contact surfaces 136 of the biasing arms 130 in a distal direction 152.

As the contact surfaces 136 are repositioned in a distal direction 152, the contact surfaces 136 contact the annular ridge 116 and advance the catheter adapter 110 in a distal direction 152 relative to the needle hub 120. Accordingly, the beveled portion 162 of the needle 160 is withdrawn, or hooded within the catheter tube 114. In some embodiments, the length of the biasing arms 130 is selected so as to accurately hood the beveled portion 162 of the needle 160 thereby preventing overhooding or underhooding inaccuracies. In other embodiments, the length of the biasing arms 130 is selected so as to create sufficient force in the distal direction between the needle hub 120 and the catheter adapter 110 when the biasing arms 130 are actuated by the user. This force is necessarily sufficient to overcome the interaction between the feature 126 and the detent 128 thereby allowing the catheter adapter 110 to move in a distal direction 152 relative to the needle hub 120.

In some embodiments, the inserted portion 124 of the needle hub 120 and the inner surface 146 of the catheter adapter 110 comprise a plurality of features and detents (not shown). As such, the position of the beveled portion 162 of the needle 160 is controlled and maintained based on interactions between the various features and detents. For example, in some embodiments the inserted portion 124 of the needle hub 120 comprises a feature 126 and the inner surface 146 of the catheter adapter 110 comprises a first and second detent (not shown). Prior to catheterization, the feature 126 is engaged with the first detent (not shown) whereby the beveled portion 162 of the needle 160 is positioned and maintained beyond the tip portion 140 of the catheter tube 114. Upon compression of the biasing arms 130, the feature 126 is displaced from the first detent (not shown) such that the catheter adapter 110 is free to move in a distal direction 152. Once the beveled portion 162 of the needle 160 is hooded, the feature 126 engages the second detent (not shown) thereby preventing further movement of the catheter adapter 110 in the distal direction 152. Thus, the interaction between the feature 126 and the second detent prevents overhooding of the needle 160 during catheterization.

Once fully actuated, the hooded needle 160 and catheter tube 114 are then advanced into the vasculature of the patient without fear of perforating the patient's vein. The catheterization process is then completed by removing the needle hub 120 from the catheter adapter 110 such that the vasculature of the patient and the lumen 142 of the catheter tube 114 are in fluid communication.

Figure 3A:
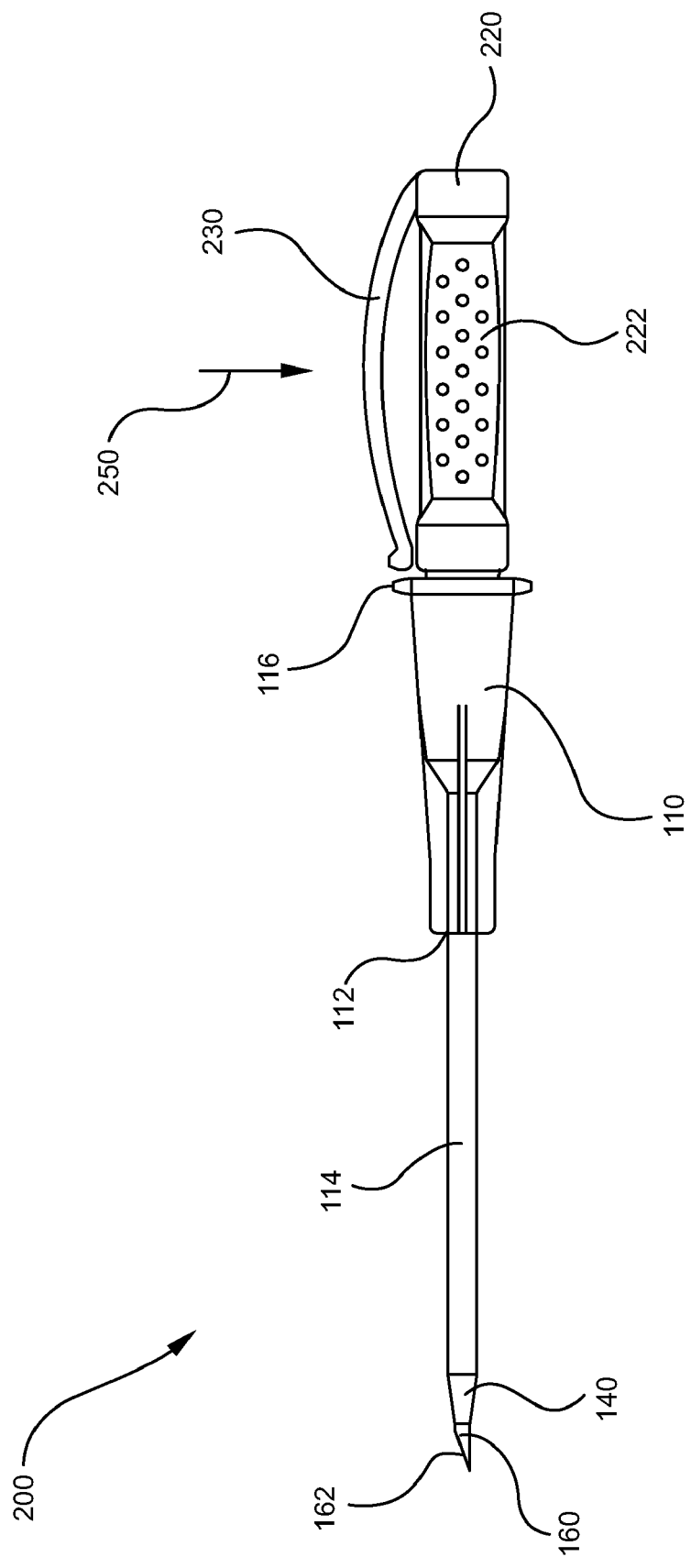
FIG. 3A is a side view of an intravenous catheter device having a single biasing arm in accordance with a representative embodiment of the present invention.

Referring now to FIG. 3A, a side view of an intravenous catheter device 200 is shown. As previously discussed, some embodiments of the present invention comprise a single biasing arm 230. As with those embodiments comprising a plurality of biasing arms, a single biasing arm 230 is provided as a means for hooding the beveled portion 162 of an introducer needle 160 during the catheterization process. In some embodiments, biasing arm 230 is positioned such that a user may grasp or pinch gripping surface 222 of the needle hub 220 between a thumb and opposing finger, and compress 250 or actuate the biasing arm 230 with a second opposing finger, as shown in FIG. 3B.

Figure 3B:
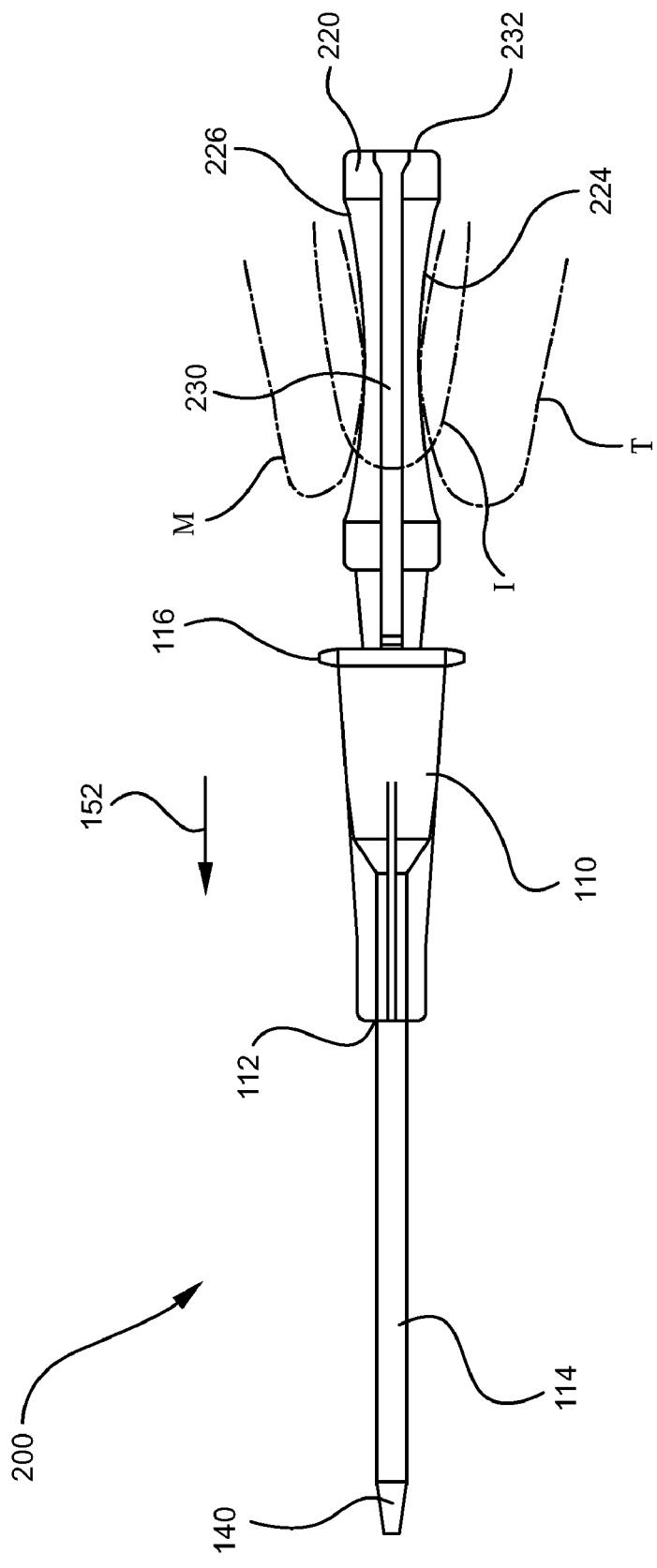
FIG. 3B is a top view of an intravenous catheter device having a single biasing arm, following activation of the biasing arm in accordance with a representative embodiment of the present invention.

With continued reference to FIG. 3B, a top view of the intravenous catheter device 200 is shown, following actuation of the biasing arm 230. For this embodiment, a first gripping surface 224 and a second gripping surface 226 are pinched between a user's thumb and a user's middle finger, respectively. Once the beveled portion 162 of the introducer needle 160 accesses the patient's vasculature, biasing arm 230 is actuated by compressing the arm 230 with the user's index finger, thereby temporarily removing the arch or non-linear profile of the arm 230. By temporarily removing the non-linear profile of the biasing arm 230, the distance between the first end 232 and the second end 234 of the arm 230 is increased thereby repositioning the contact surface 236 of the biasing arm 230 in a distal direction 152.

As the contact surface 236 is repositioned in a distal direction 152, the contact surface 236 contacts the annular ridge 116 and advances the catheter adapter 110 in a distal direction 152 relative to the needle hub 220. Accordingly, the beveled portion 162 of the needle 160 is withdrawn, or hooded within the catheter tube 114, as previously discussed.

Figure 4:
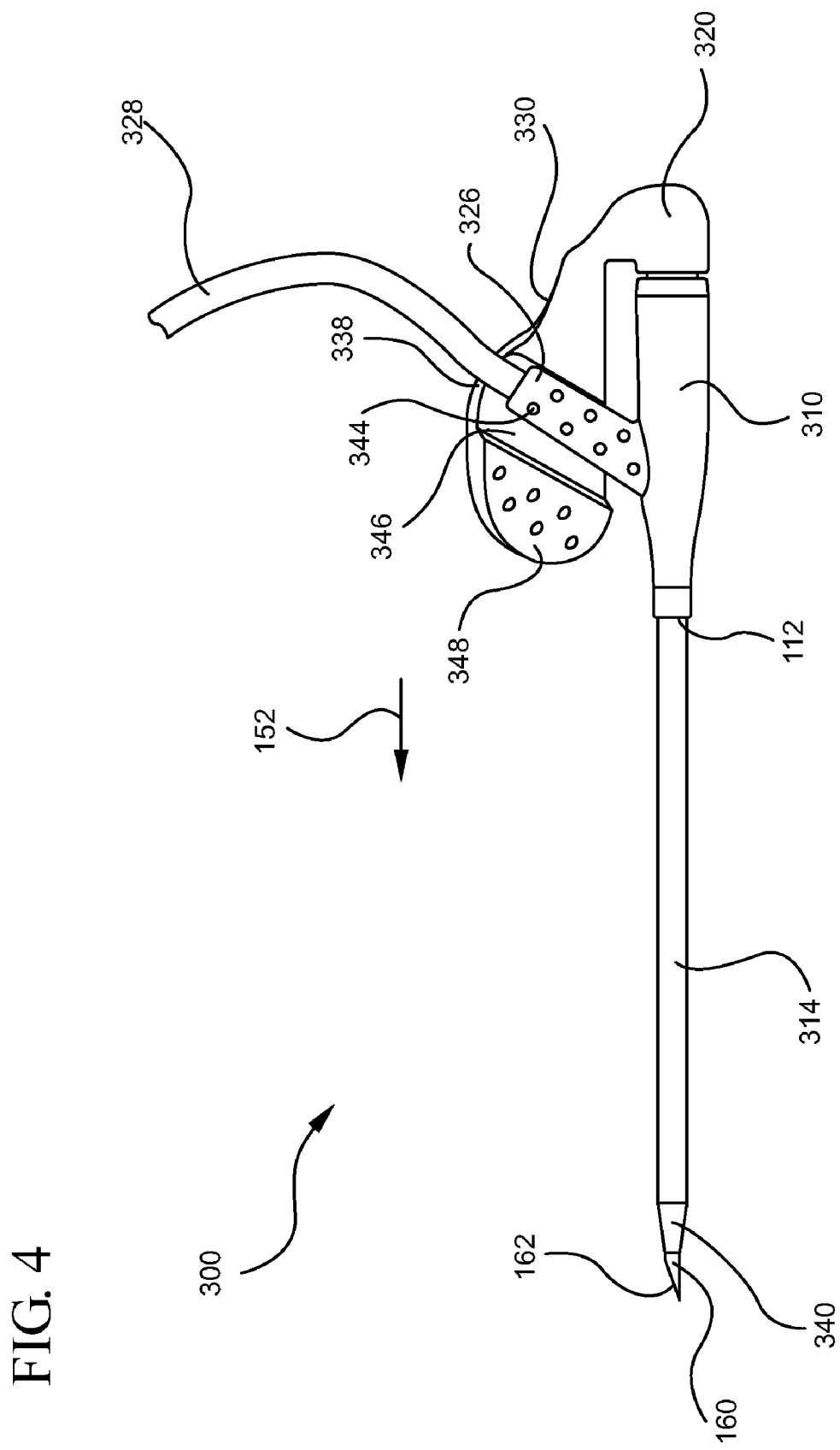
FIG. 4 is a top view of an intravenous catheter device having a paddle grip biasing arm in accordance with a representative embodiment of the present invention.

Referring now to FIG. 4, an intravenous catheter device 300 is shown in accordance with a preferred embodiment of the present invention. In some embodiments, the catheter adapter 310 further includes a y-port 326 whereby a fluid is delivered to the catheter tube 314 via a section of intravenous tubing 328. Y-port 326 generally comprises a molded extension of catheter adapter 310 whereby the inner lumen of the catheter adapter 310 and the intravenous tubing 328 are in fluid communication. In some embodiments, an external surface of the y-port 326 comprises a texture or coating 344. Coating 344 provides a gripping surface configured to support a portion of a user's thumb when gripping the catheter device 300 during the catheterization process.

Catheter device 300 further includes a needle hub 320. As with previous embodiments, needle hub 320 provides a base means for securing a non-working end of introducer needle 160. A portion of needle hub 320 is housed within the inner lumen of catheter adapter 310, such that needle hub 320 and catheter adapter 310 form an integral device. Furthermore, the interaction between needle hub 320 and catheter adapter 310 is configured to expose the beveled portion 162 of the introducer needle 160 prior to actuating the biasing arm 330 of the device 300. As such, the beveled portion 162 of the introducer needle 160 is available to assist in gaining access to the vasculature of a patient.

Biasing arm 330 comprises a paddle-shaped extension or appendage of needle hub 320. In some embodiments, biasing arm 330 comprises a paddle grip. Biasing arm 330 is configured to extend in a distal direction 150 generally parallel to length of the catheter adapter 310. A middle portion 338 of biasing arm 330 comprises a channel or groove 346 configured to slidably receive y-port 326 of the catheter adapter 310. Thus, the width, length and depth of groove 346 are carefully selected to permit controlled movement of the y-port 326 within the groove 346. For example, in some embodiments the dimensions of groove 346 are selected to achieve proper hooding of the needle tip 162, thereby preventing overhooding or underhooding inaccuracies.

A terminal end of the biasing arm 330 further comprises a texture or coating 348. Coating 348 provides a gripping surface configured to support a second portion of a user's thumb when gripping the catheter device 300. In some embodiments, coatings 344 and 348 are configured to support a user's thumb during the catheterization process. In other embodiments, coatings 344 and 348 are excluded from catheter device 300. For these embodiments, exposed, yet uncoated surfaces of y-port 326 and biasing arm 330 are provided to support a user's thumb during catheterization. Finally, in some embodiments a surface of the biasing arm 330 opposite groove 346 is provided to support opposing fingers of the user's grip, as shown and discussed in FIG. 6, below.

Figure 5A:
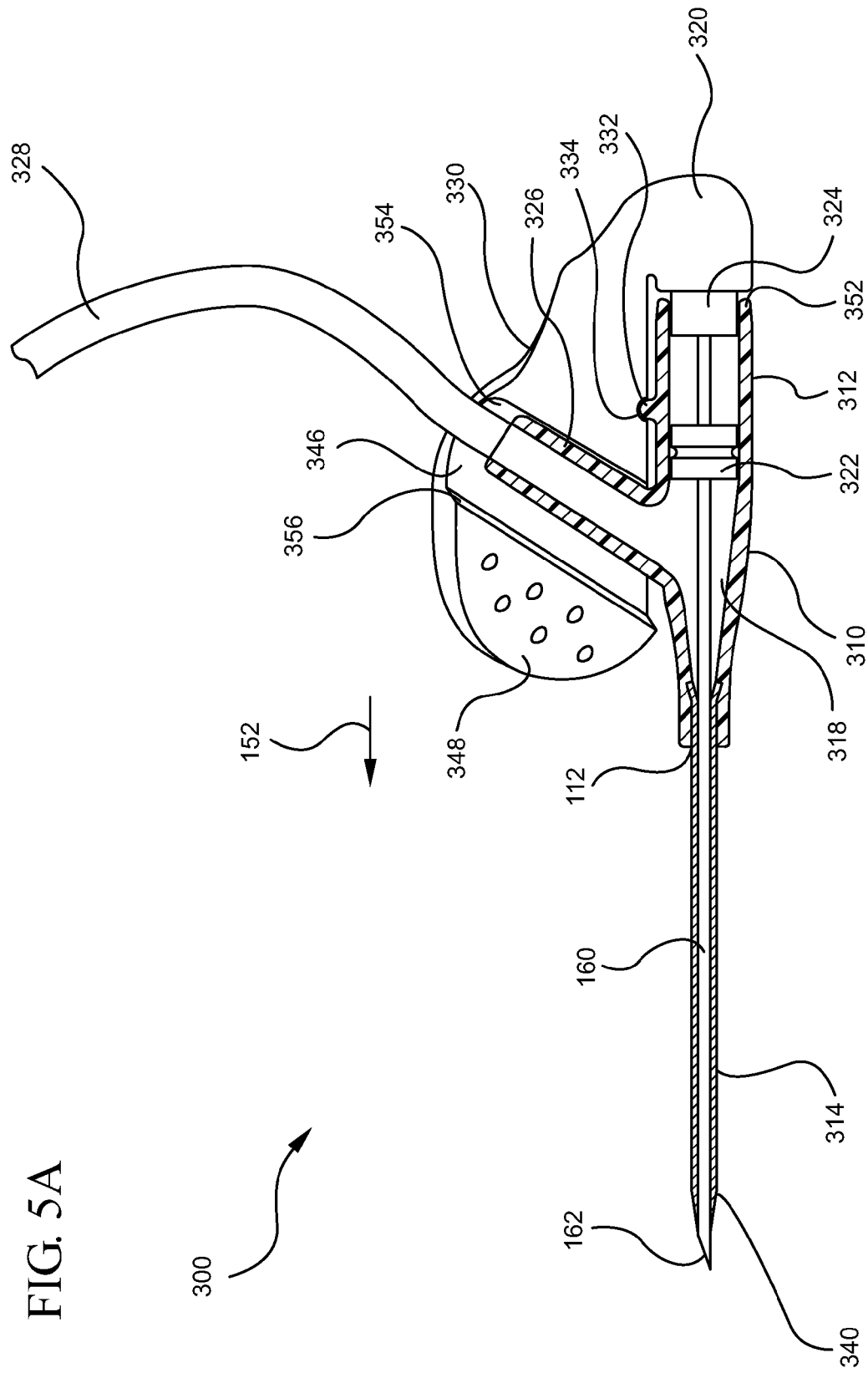
FIG. 5A is a partial cross-section top view of an intravenous catheter device having a paddle grip biasing arm in accordance with a representative embodiment of the present invention.

Referring now to FIG. 5A, partially cross-sectioned catheter device 300 is shown prior to catheterization, wherein biasing arm 330 is in an unactuated position. Prior to being actuated, biasing arm 330 is positioned such that inserted portion 324 is fully inserted within the inner lumen 318. Generally, a stopper 322 is positioned within inner lumen 318 between the inserted portion 324 of needle hub 320 and the y-port 326. As such, fluid is prevented from exiting the catheter adapter 310 via the proximal end 352. Accordingly, fluid flow is restricted to the catheter tube 314, the intravenous tubing 328 and the intervening portion of inner lumen 318.

The unactuated position of biasing arm 330 is characterized by the exposed position of the beveled portion 162 of introducer needle 160. In some embodiments, the unactuated position of biasing arm 330 is further characterized by the position of y-port 326 within groove 346. For example, in some embodiments the unactuated position of biasing arm 330 is achieved when y-port 326 is positioned in the proximal half 354 of groove 346, as shown. As positioned, inserted portion 324 is maximally inserted into catheter adapter 310 thereby advancing beveled portion 162 of introducer needle 160 beyond the tip 340 of catheter tube 314. The unactuated position of catheter device 300 is maintained as the user's thumb simultaneously contacts textures 344 and 348, thereby bridging the catheter adapter 310 and the needle hub 320 via the gripping surfaces of y-port 326 and biasing arm 330. Opposing fingers further grasp an opposing surface of the biasing arm 330 such that the device 300 is held via a pinch-grip.

In some embodiments, the outer surface 312 of the catheter adapter 310 further includes a feature 332 for engaging a detent 334 located on the biasing arm 330. The interaction between the feature 332 and the detent 128 prevents premature hooding of the needle 160 during catheterization. The interaction further prevents premature hooding of the needle during assembly, packaging and shipment of the intravenous catheter device 300. In some embodiments, the outer surface 312 of the catheter adapter 310 is modified to include a detent (not shown) configured to receive a feature (not shown) formed on the biasing arm 330. One having skill in the art will appreciate that the interaction between a desired feature and a compatible detent will be sufficiently resilient to prevent premature hooding of the needle 160, yet be capable of defeat by user manipulation of the y-port 326 in the distal direction 152.

Figure 5B:
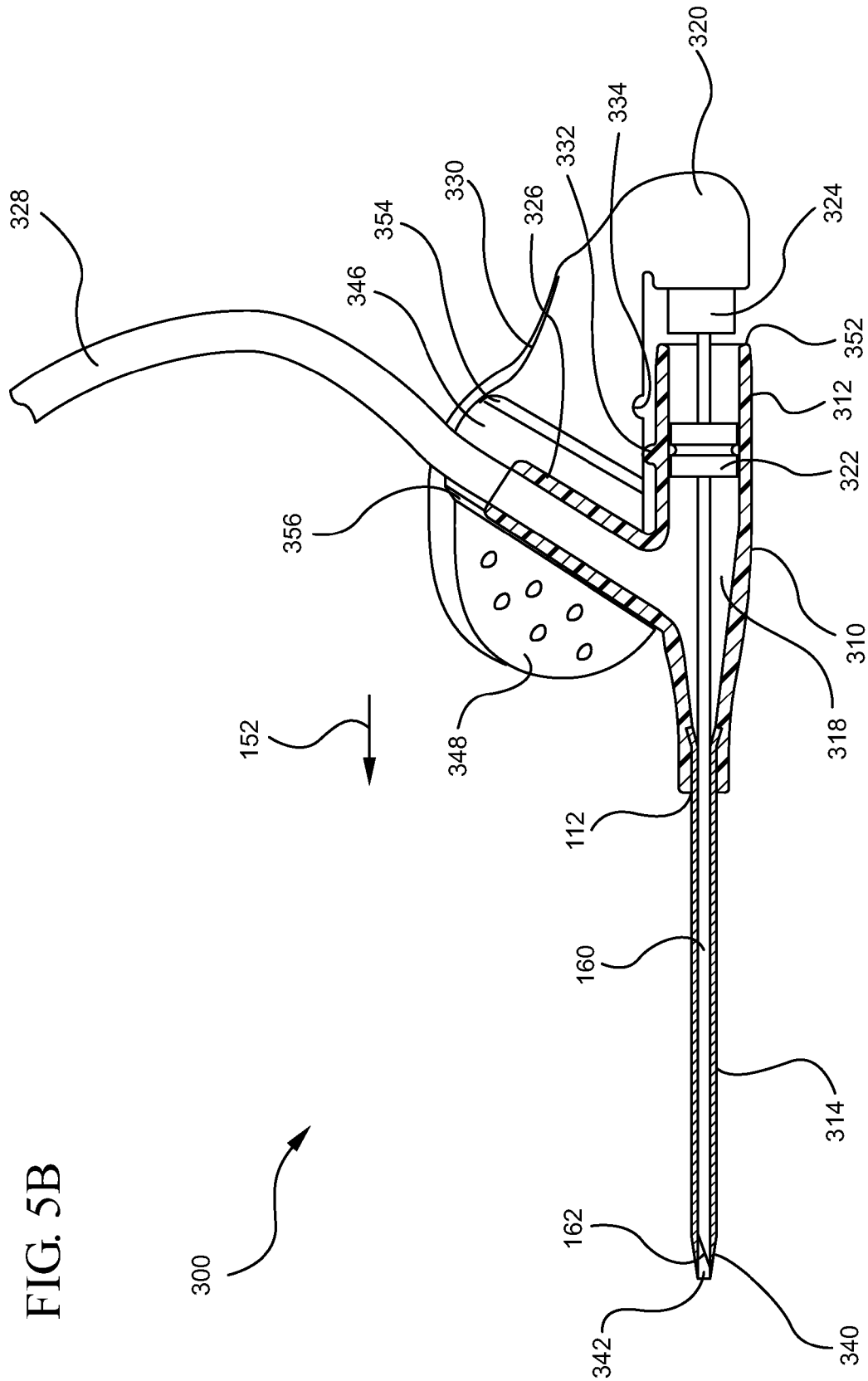
FIG. 5B is a partial cross-section top view of an intravenous catheter device having a paddle grip biasing arm following actuation of the biasing arm in accordance with a representative embodiment of the present invention.

Referring now to FIG. 5B, partially cross-sectioned catheter device 300 is shown following actuation of biasing arm 330. Following actuation of biasing arm 330, inserted portion 324 of needle hub 320 is mostly removed from catheter adapter 310, thereby causing beveled portion 162 of introducer needle 160 to be hooded within catheter tube 314. In some embodiments, the actuated position of biasing arm 330 is further characterized by the position of y-port 326 within groove 346. For example, in some embodiments the actuated position of biasing arm 330 is achieved when y-port 326 is positioned in the distal half 356 of groove 346, as shown. As positioned, inserted portion 324 is only partially inserted into catheter adapter 310 thereby withdrawing beveled portion 162 of introducer needle 160 into the lumen 342 of catheter tube 314. The actuated position of catheter device 300 is achieved by shifting or translocating y-port 326 from the proximal half 354 to the distal half 356 of groove 346. In some embodiments this is achieved by temporarily releasing the user's thumb from the textured surface 348 of the biasing arm 330 and simultaneously advancing the y-port 326 in a distal direction 152. Once the beveled portion 162 of the needle 160 is hooded, the actuated position of the biasing arm is maintained as the user's thumb again contacts the textured surface 348 of the biasing arm 330, such that the user's thumb simultaneously contacts textures 344 and 348, thereby bridging the catheter adapter 310 and the needle hub 320 via the gripping surfaces of y-port 326 and biasing arm 330.

In some embodiments, the outer surface 312 of the catheter adapter 310 and the biasing arm 330 comprise a plurality of features and detents (not shown). As such, the position of the beveled portion 162 of the needle 160 is controlled and maintained based on variable interactions between the various features and detents. For example, in some embodiments the outer surface 312 of the catheter adapter 310 comprises a feature 332 and an adjacent surface of the biasing arm 330 comprises a first detent and a second detent (not shown). Prior to catheterization, the feature 332 is engaged with the first detent (not shown) whereby the beveled portion 162 of the needle 160 is positioned and maintained beyond the tip portion 340 of the catheter tube 314. Upon translating the y-port 326 in a distal direction 152 relative to the biasing arm 330, the feature 332 is displaced from the first detent (not shown) such that the catheter adapter 310 is free to move in the distal direction 152. Once the beveled portion 162 of the needle 160 is hooded, the feature 332 engages the second detent (not shown) thereby preventing further movement of the catheter adapter 310 in the distal direction 152. In some embodiments, the interaction between the feature 332 and the second detent corresponds to a position of the y-port 326 within the distal half 356 of the channel 346. Thus, the interaction between the feature 332 and the second detent prevents overhooding of the needle 160 during catheterization.

Figure 6A:
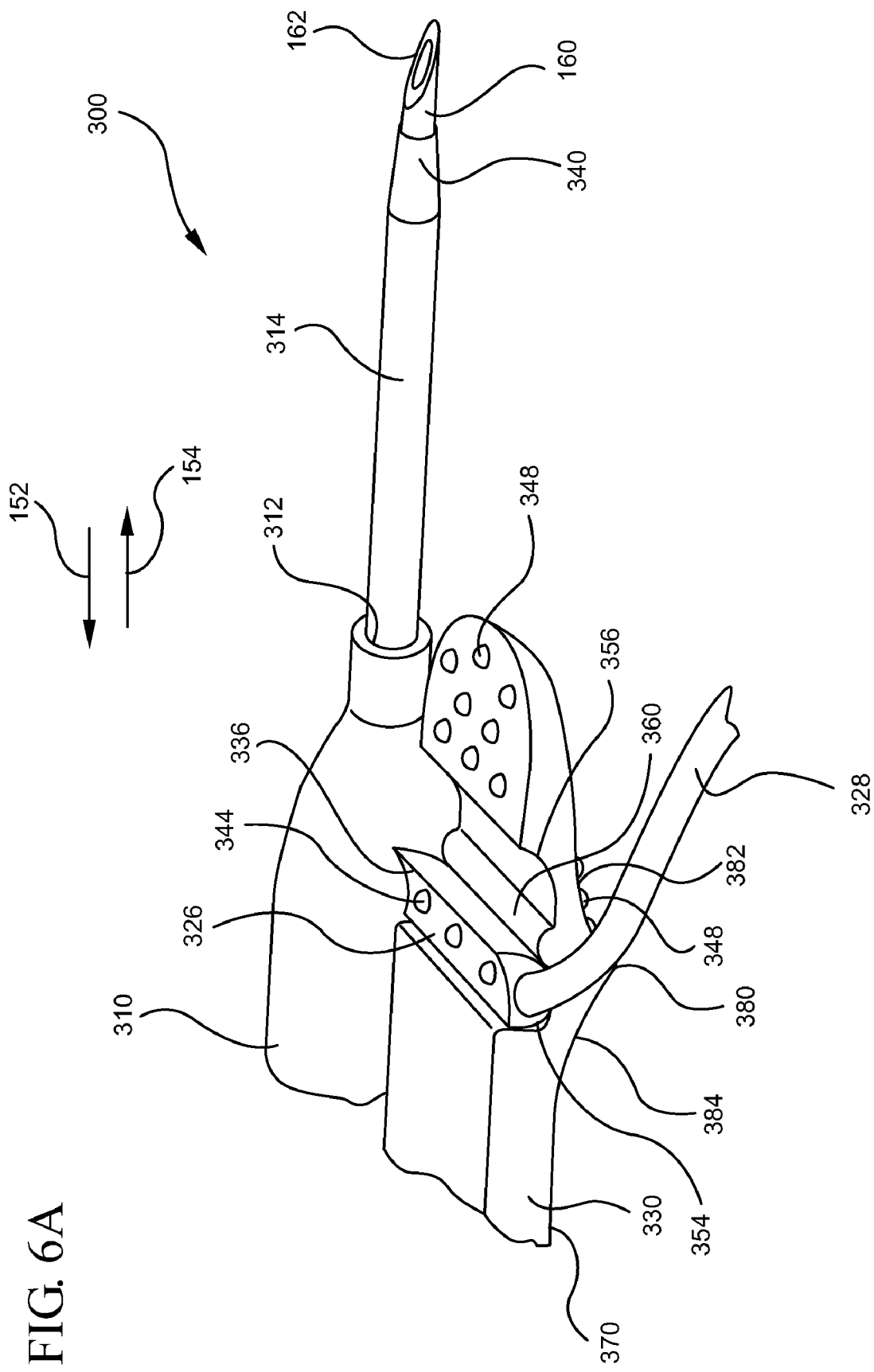
FIG. 6A is a perspective view of a portion of an intravenous catheter device having a paddle grip biasing arm prior to actuation of the biasing arm in accordance with a representative embodiment of the present invention.

With reference to FIG. 6A, a perspective side view of a partial catheter device 300 is shown prior to actuation of the biasing arm 330. In some embodiments, y-port 326 is configured to accommodate a user's thumb in gripping and controlling the position of the catheter adapter 310 relative to the biasing arm 330. In particular, some configurations of y-port 326 include a flared or raised distal edge 336. Edge 336 provides a surface against which the user's thumb may apply a perpendicular force to the y-port 326 to reposition the catheter adapter 310 in a distal direction 152. Similarly, an opposing side 370 of biasing arm 330 is modified to include an ergonomic or gripping feature 380. Gripping feature 380 is configured to provide a first gripping surface 382 to accommodate a first opposing finger of the user, and a second gripping surface 384 to accommodate a second opposing finger of the user. Thus, gripping surfaces 382 and 384 provide surfaces against which the user's opposing fingers may grasp and apply a perpendicular force to the gripping feature 380 to reposition the biasing arm 330 in a proximal direction 154. In some embodiments, gripping surface 382 is further modified to include a texture or coating 348 to increase friction between the user's first opposing finger and the first gripping surface 382. In other embodiments, gripping surface 384 also comprises a texture or coating material (not shown).

The protruding nature of feature 380 provides surfaces 382 and 384 against which a user may support the biasing arm 330 during the catheterization process. Additionally, gripping surfaces 382 and 384 provide surfaces by which the user may immobilize the position of the biasing arm 330 while shifting or translocating y-port 326 from the proximal half 354 to the distal half 356 of groove 346. Thus, in some embodiments ergonomic feature 380 provides both a gripping surface and a biasing surface to aid in gripping and actuating the biasing arm 330 of the intravenous catheter device 300.

In some embodiments, groove 346 of the biasing arm 330 is further modified to include a feature 360 designed to prevent premature translation of the y-port 326 within the groove 346 during catheterization. In some embodiments, feature 360 comprises a ridge or raised surface of the groove 346. Feature 360 is generally positioned so as to divide groove 346 into a proximal half 354 and a distal half 356. Prior to insertion of the catheter 314 into a patient, y-port 326 is positioned within the proximal half 354 of the groove 346 such that the beveled portion 162 of the needle 160 extends distally beyond the tip 340 of the catheter tube 314. Feature 360 maintains the position of y-port 326 within the proximal half 352 thereby allowing a user to insert the catheter 314 and needle 160 using a forward motion, while preventing premature hooding of the needle's bevel 162. One of skill in the art will appreciate that the size and dimensions of feature 360 are selected to prevent unintended hooding of needle 160. One of skill in the art will further appreciate that the size and dimensions of feature 360 are selected to permit a user to one-handedly bypass the feature 360, whereby y-port 326 is repositioned within the distal half 356 of the groove 346 and hood the needle 160 following insertion of the tip 340 of the catheter tube 314.

Figure 6B:
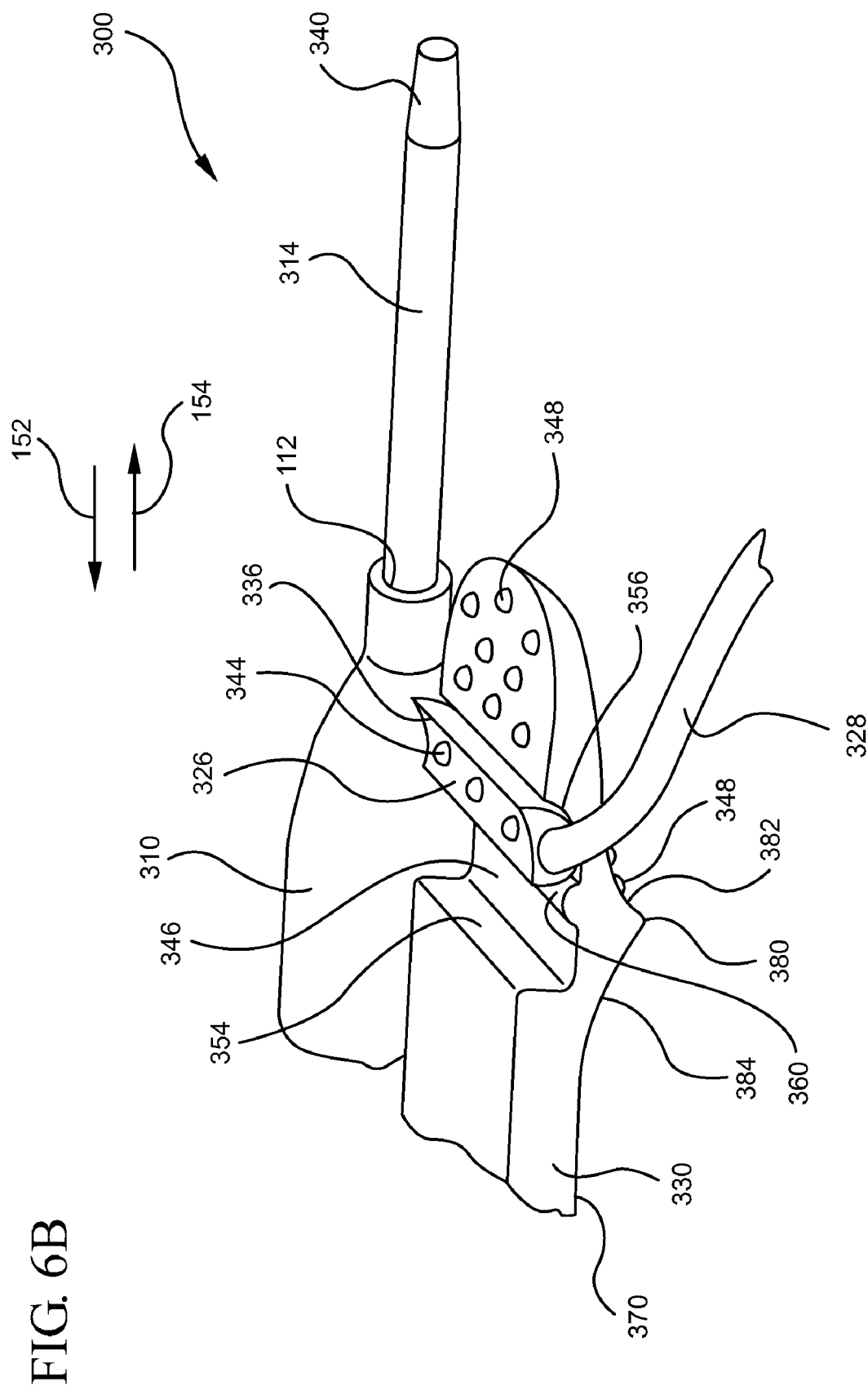
FIG. 6B is a perspective view of a portion of an intravenous catheter device having a paddle grip biasing arm following actuation of the biasing arm in accordance with a representative embodiment of the present invention.

With reference to FIG. 6B, a perspective side view of a partial catheter device 300 is shown following actuation of the biasing arm 330. In particular, FIG. 6B demonstrates catheter device 300 following translation of the y-port 326 from the proximal half 354 of the groove 346 to the distal half 356. As previously discussed, following insertion of the needle 160 and the tip 340 of the catheter 314 within the patient, the y-port 326 of the catheter adapter 310 is repositioned within the groove 346 resulting in the needle 160 being hooded within the catheter 314. This repositioning occurs as a result of y-port 326 being slid forward in a distal direction 152 while simultaneously sliding the biasing arm backward in a proximal direction 154. In other words, the needle tip 162 is hooded as a result of a user exerting a forward or distal force 152 on the flared edge 336 of the y-port 326 while simultaneously exerting a backward or proximal force 154 of the gripping feature 380 of the biasing arm 330. The opposing surfaces of the y-port 326, the groove 346 and the features 360 serve as complimentary sliding surfaces to facilitate a user in hooding the beveled portion 162 of the needle 160.

Following insertion of the catheter tube 314, the biasing arm 330 is axially rotated such that the y-port 326 is disengaged from groove 346. Once disengaged, the needle hub 320 and biasing arm 330 are withdrawn in a proximal direction whereby the needle hub 320 and introducer needle 160 are entirely removed from catheter adapter 310. The needle hub 320, needle 160 and biasing arm 330 are then disposed in a safe manner, as is customary.

The present invention may be embodied in other specific forms without departing from its structures, methods, or other essential characteristics as broadly described herein and claimed hereinafter. For example, one having skill in the art will appreciate that embodiments of the present invention may further include a needle retaining device or a safety feature to prevent exposure to the needle and/or fluids associated therewith. Thus, the described embodiments and examples are all to be considered in every respect as illustrative only, and not as being restrictive. The scope of the invention is, therefore, indicated by the appended claims, rather than by the foregoing description. All changes that come within the meaning and range of equivalency of the claims are to be embraced within their scope.

What is claimed is:

1. An intravenous catheter device, comprising:
    a catheter adapter having a first end and a second end, the first end supporting a catheter tube, and the second end having an opening;
    a needle partially disposed within the catheter tube, a tip portion of the needle extending beyond a tip of the catheter tube, the needle further having a body extending through the catheter tube and into the catheter adapter;
    a needle hub partially disposed within the opening of the second end of the catheter adapter, a portion of the needle body being coupled to the needle hub; and
    an arm having a first end coupled to the needle hub and a second end in contact with a surface of the catheter adapter, wherein upon actuating the arm, the arm is moved toward a position increasing the distance between the first and second ends of the arm and applying a force against the surface of the catheter adapter that repositions the catheter adapter relative to the needle hub such that the tip portion of the needle is hooded within the catheter tube.

2. The device of claim 1, wherein the arm comprises a plurality of arms, wherein in an arched, non-linear position the length of the arms is greater than the distance between the first and second ends.

3. The device of claim 2, wherein the plurality of arms includes a first arm and a second arm, the first arm having a first contact to contact a first surface of the catheter adapter, and the second arm having a second contact to contact a second surface of the catheter adapter.

4. The device of claim 1, further comprising a detent and protruding feature between the needle hub and the catheter adapter, wherein the force against the surface of the catheter adapter overcomes the force retaining the protruding feature within the detent.

5. A method for manufacturing an intravenous catheter device, the method comprising:
providing a catheter adapter having a first end and a second end, the first end supporting a catheter tube, and the second end having an opening;
partially disposing a needle within the catheter tube, a tip portion of the needle extending beyond a tip of the catheter tube, the needle further having a body extending through the catheter tube and into the catheter adapter;
partially disposing a needle hub within the opening of the second end of the catheter adapter, a portion of the needle body being coupled to the needle hub; and
providing an arm having a first end coupled to the needle hub and a second end in contact with a surface of the catheter adapter, wherein upon actuating the arm, the arm is moved toward a position increasing the distance between the first and second ends of the arm and applying a force against the surface of the catheter adapter that repositions the catheter adapter relative to the needle hub such that the tip portion of the needle is hooded within the catheter tube.

6. The method of claim 5, further comprising providing a plurality of arms, wherein in an arched, non-linear position the length of the arms is greater than the distance between the first and second ends.

7. The method of claim 6, wherein the plurality of arms includes a first arm and a second arm, the first arm having a first contact to contact a first surface of the catheter adapter, and the second arm having a second contact to contact a second surface of the catheter adapter.

8. The method of claim 5, further comprising providing a detent and protruding feature between the needle hub and the catheter adapter, wherein the force against the surface of the catheter adapter overcomes the force retaining the protruding feature within the detent.

9. A system for hooding a tip of an introducer needle of an intravenous catheter device during intravenous procedures, comprising:
an intravenous catheter device having a needle hub slidably inserted within a portion of a catheter adapter, an introducer needle coupled to the needle hub and extending through an inner lumen of a catheter tube coupled to the catheter adapter, a tip of the introducer needle extending distally beyond a tip of the catheter tube;
an arm coupled to at least one of the needle hub and the catheter adapter, the arm being biased in an arched, non-linear position in which the length of the arms is greater than the distance between the first and second ends, wherein upon actuating the arm, the arm is moved toward a linear position, increasing the distance between the first and second ends of the arm and applying a force against the surface of the catheter adapter that repositions the catheter adapter relative to the needle hub such that the tip portion of the needle is hooded within the catheter tube.

10. The system of claim 9, wherein the arm comprises a plurality of arms.

11. The system of claim 10, wherein the plurality of arms includes a first arm and a second arm, the first arm having a first contact to contact a first surface of the catheter adapter, and the second arm having a second contact to contact a second surface of the catheter adapter.

12. The system of claim 9, further comprising a detent and protruding feature between the needle hub and the catheter adapter, wherein the force against the surface of the catheter adapter overcomes the force retaining the protruding feature within the detent.

* * * * *